(12) United States Patent
Thorp et al.

(10) Patent No.: US 9,173,725 B2
(45) Date of Patent: Nov. 3, 2015

(54) DENTAL NOZZLE

(75) Inventors: Chris Thorp, Manchester (GB); Alan Julian Segal, Cheshire (GB)

(73) Assignee: Astek Innovations Limited, Altrincham, Cheshire (GB)

(*) Notice: Subject to any disclaimer, the term of this patent is extended or adjusted under 35 U.S.C. 154(b) by 133 days.

(21) Appl. No.: 13/703,113

(22) PCT Filed: May 27, 2011

(86) PCT No.: PCT/GB2011/051008
§ 371 (c)(1),
(2), (4) Date: Dec. 10, 2012

(87) PCT Pub. No.: WO2011/154718
PCT Pub. Date: Dec. 15, 2011

(65) Prior Publication Data
US 2013/0078597 A1  Mar. 28, 2013

(30) Foreign Application Priority Data

Jun. 9, 2010 (GB) .................................. 1009644.4
Mar. 9, 2011 (GB) .................................. 1103947.6

(51) Int. Cl.
*A61C 17/02* (2006.01)
*A61C 17/022* (2006.01)

(52) U.S. Cl.
CPC ............ *A61C 17/0202* (2013.01); *A61C 17/022* (2013.01); *A61C 17/0214* (2013.01)

(58) Field of Classification Search
CPC ........... A61C 17/0202; A61C 17/0214; A61C 17/022
USPC .............. 433/80; 222/478, 479, 566; 427/2.1, 427/421.1

See application file for complete search history.

(56) References Cited

U.S. PATENT DOCUMENTS

| 2,325,495 | A | * | 7/1943 | Ferguson | 239/403 |
| 3,069,099 | A | * | 12/1962 | Graham | 239/453 |
| 3,093,315 | A | * | 6/1963 | Sata et al. | 239/432 |
| 3,727,310 | A | | 4/1973 | Baker | |
| 4,284,239 | A | * | 8/1981 | Ikeuchi | 239/8 |
| 4,415,123 | A | * | 11/1983 | Ikeuchi | 239/425 |
| 4,472,141 | A | * | 9/1984 | Dragan | 433/90 |
| 4,783,008 | A | * | 11/1988 | Ikeuchi et al. | 239/421 |

(Continued)

FOREIGN PATENT DOCUMENTS

| DE | 10 2007 00734 | 8/2008 |
| FR | 1 285 767 | 2/1962 |

OTHER PUBLICATIONS

Machine English Translation for FR 1285767, pp. 1-5.*

(Continued)

*Primary Examiner* — Cris L Rodriguez
*Assistant Examiner* — Hao D Mai
(74) *Attorney, Agent, or Firm* — Renner, Otto, Boisselle & Sklar, LLP

(57) ABSTRACT

A nozzle tip for a three-way syringe device, including a co-axial tube assembly having attachment feature adapted for releasable attachment of the nozzle tip to a syringe device, and wherein the tube assembly includes an outer tube and an inner tube, the inner tube having an end section including an inclined outlet face, and wherein the inner tube is tight-fit against the interior surface of the outer tube. The nozzle tip is included in a dental apparatus including a three-way syringe device.

16 Claims, 5 Drawing Sheets

(56) References Cited

U.S. PATENT DOCUMENTS

Figure 1:
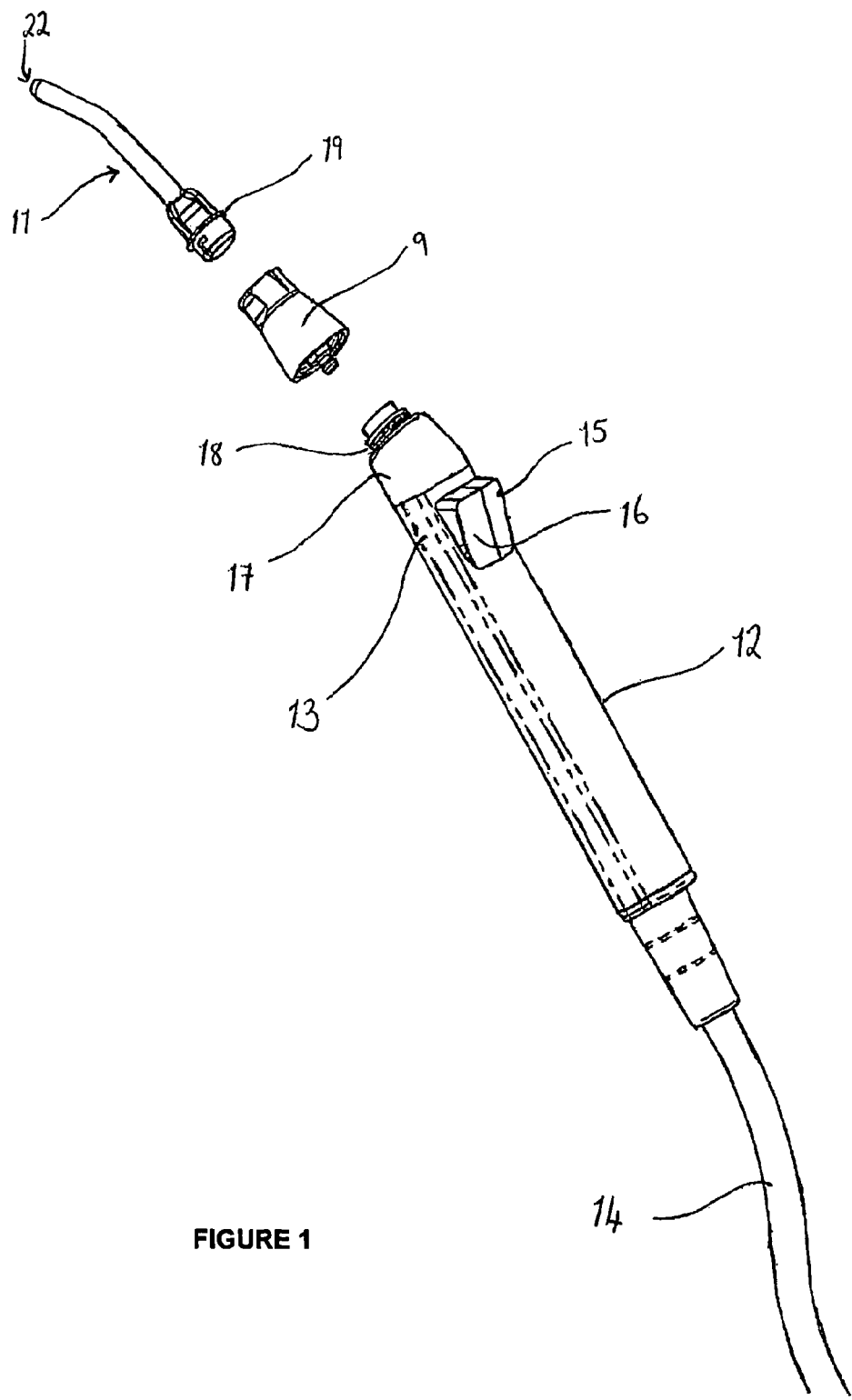

| | | | |
|---|---|---|---|
| 5,486,676 A * | 1/1996 | Aleshin | 219/121.63 |
| 5,820,373 A * | 10/1998 | Okano et al. | 433/80 |
| 6,824,077 B2 * | 11/2004 | De Laforcade | 239/333 |
| 9,033,194 B1 * | 5/2015 | Grabowski et al. | 222/566 |
| 2011/0011899 A1 * | 1/2011 | Yeates | 222/566 |

OTHER PUBLICATIONS

International Search Report for corresponding patent application No. PCT/GB2011/051008 dated Oct. 4, 2011.

* cited by examiner

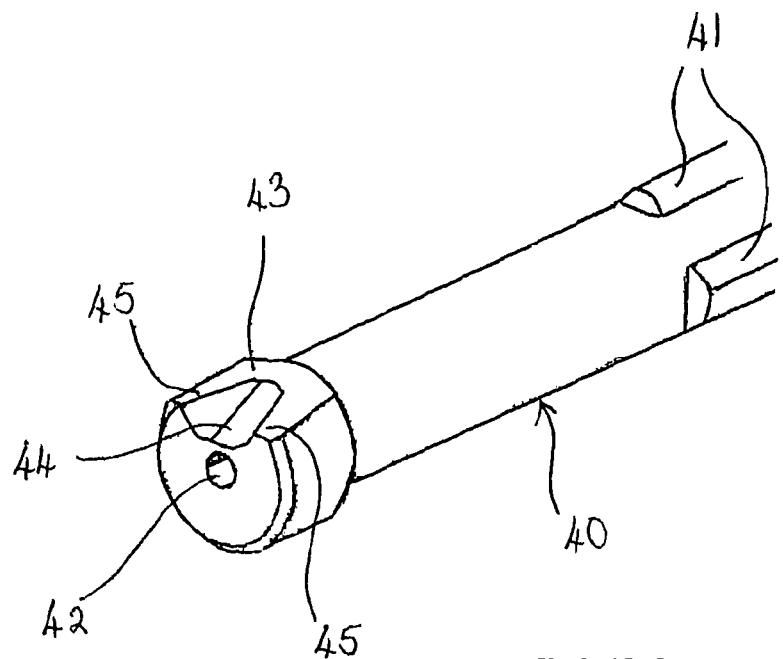
FIGURE 8
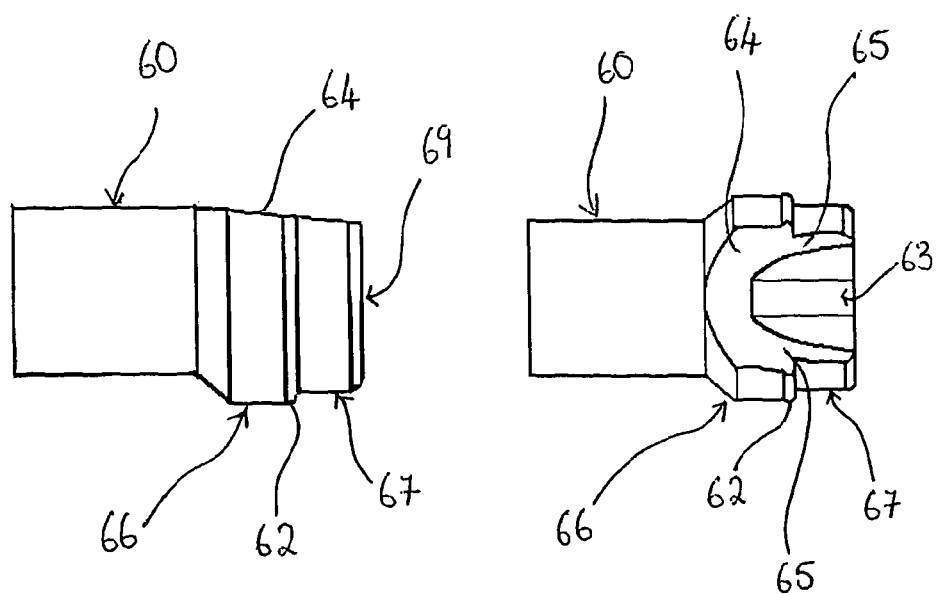
FIGURE 9          FIGURE 10

DENTAL NOZZLE

This application is a national phase of International Application No. PCT/GB2011/051008 filed May 27, 2011 and published in the English language.

The present invention relates to a dental apparatus, and in particular to dental syringe apparatus having a nozzle tip for providing a jet of air, liquid, or a mixture thereof to a patient undergoing dental treatment.

Dental syringes which deliver air, water, or air/water mixtures (also known as three-way syringes) are used for cleaning the mouth of a patient prior to and during dental procedures. These dental syringes are able to deliver water or air at high pressure at specific small areas of the mouth.

The typical dental syringe apparatus comprises a hand-held appliance to which a supply of air and a supply of water, both under pressure, are supplied, and has a nozzle assembly or tip at the operating end thereof. Such nozzle assembly or nozzle tip comprises a coaxial tube assembly which is secured on the end of the three-way syringe apparatus.

Both inner and outer tubes of the nozzle tip are of plastics or metals. Since the inner tube must be supported within the outer tube whilst allowing flow through the outer tube, the nozzle tip may be relatively costly to produce.

The three-way syringe may also come in to contact with the patient's mouth during use, and therefore to prevent contamination or cross-infection between patients disposable syringe tips have become available.

GB 2213732 describes a disposable syringe tip for use on air/water dental syringes. The disclosed disposable tip can be used on three way dental syringes during dental procedures to clean and dry areas of the patient's mouth by selectably delivering a jet of water for rinsing, a jet of air for drying, and an atomised spray of both water and air. However, a disposable tip would advantageously work with all types of dental chairs. There is a particular problem with the increasing range of dental chairs becoming available, with some performance problems being identified. This is particularly the case for certain syringes and dental chairs which operate at lower air pressure (around 40 psi) when compared to the more typical air pressure of 60 psi. When this disposable tip is used with lower pressure chairs, it can be the case that it exhibits a less than desired performance in terms of the velocity of the air jet and the quality of the atomised spray produced.

It is an object of the present invention to provide a dental apparatus which is capable of good performance at both higher and lower pressures of water and air, and may be disposable after each occasion of use in order to prevent contamination.

According to a first aspect of the present invention there is provided a dental apparatus comprising a nozzle tip for a three-way syringe device, said nozzle tip comprising a co-axial tube assembly having attachment means adapted for releasable attachment of said nozzle tip to a syringe device, and wherein said tube assembly comprises an outer tube and an inner tube, said inner tube having an end section comprising an inclined outlet face, and wherein the inner tube is tight-fit against the interior surface of the outer tube.

According to a second aspect of the present invention there is provided nozzle tip for a three-way syringe device, said nozzle tip comprising a co-axial tube assembly having attachment means adapted for releasable attachment of said nozzle tip to a syringe device, and wherein said tube assembly comprises an outer tube and an inner tube, said inner tube having an end section comprising an inclined outlet face, and wherein the inner tube is tight-fit against the interior surface of the outer tube.

With this arrangement, the nozzle tip can exhibit good performance in relation to both air velocity and spray quality when used with supplies of air or water at various pressures. In particular, the invention has been found to exhibit good air velocity and atomised water spray performance when used with lower pressure supplies. It has been found that this beneficial performance is provided by using a nozzle tip arrangement having an inner tube and outer tube, where the inner tube has an inclined outlet face.

The use of a tight or close fit of the inner tube to the outer tube is believed to provide sealing of the annular air flow area between the inner and outer tube at the end section. The reduction of this annular air flow area causes the air flow to be forced through and out of the nozzle tip through the inclined outlet face.

The nozzle tip may be cheaply produced so that each nozzle tip may be removed from the syringe device and discarded after use on one patient. A new uncontaminated nozzle tip can therefore be attached to the syringe device for use on the next patient. In this way, the risk of cross-infection between patients is avoided or at least substantially reduced.

The inner and outer tube may be independently formed of any suitable material. Suitable materials may include, by way of example, plastics, or metals selected from brass, stainless steel, or anodised aluminium. Preferably, the inner and outer tube may independently be formed from a plastics material. Suitable plastics materials may include, by way of example, high density polyethylene or polypropylene.

It is envisaged that the outer tube and inner tube may be separately manufactured, with subsequent assembly of the nozzle tip assembly including insertion of the inner tube in to the outer tube. Alternatively, the outer tube may be moulded onto said inner tube.

The inner tube may be formed such that it is wholly contained within the outer tube. The exposed end of the inner tube may be level with the exposed end of the outer tube.

The inner tube may comprise a hollow conduit which extends along the length of the inner tube. The hollow conduit may be centrally positioned along the length of the inner tube. The hollow conduit may have an exit point which is at the exposed end of the syringe.

The hollow conduit is preferably a conduit for water. Said conduit may therefore provide for a water flow from the end of the tip connected to the syringe along the nozzle tip to the water outlet at the exposed end of the inner tube.

It will be understood that the height of the exposed end of the inner tube represents the dimension from the inclined outlet face to the furthermost circumferal point of the inner tube, i.e. the furthermost point on the outer circumference of the inner tube. The height of the exposed end of the inner tube may be in the range from 2.00 mm to 3.20 mm. More preferably, said height may be in the range from 2.40 mm to 2.90 mm. Most preferably, said height may be in the range from 2.60 mm to 2.70 mm.

The internal diameter of the outer tube may be in the range from 3.00 mm to 3.50 mm. More preferably, said diameter may be in the range from 3.10 mm to 3.40 mm. Most preferably, said diameter may be in the range from 3.20 mm to 3.30 mm.

The internal diameter of the outer tube may vary along its length or may be constant. In an embodiment in which the diameter varies along the length of the outer tube, it will be understood that the preferred diameters detailed herein represent average values.

The diameter of the inner tube may be in the range from 3.00 mm to 3.55 mm. More preferably, said diameter may be in the range from 3.15 mm to 3.40 mm. Most preferably, said diameter may be in the range from 3.25 mm to 3.35 mm.

The diameter of the inner tube may vary along its length or may be constant. In the embodiment in which the diameter varies along the length of the inner tube, it will be understood that the preferred diameters detailed herein represent average values.

The exposed end of the inner tube may comprise a chamfered edge around the circumference, but not including the inclined outlet face.

The inner tube may comprise a plurality of flanges extending radially outward thereof. Said flanges may be located towards the end of the inner tube proximal to the syringe. Said flanges may have a clearance-fit against the inner surface of the outer tube. Alternatively, said flanges may be located in reciprocal grooves provided in the inner surface of the outer tube. Preferably there are four such flanges spaced angularly by 90° around the outer surface of the inner tube.

The inner tube may also comprise a plurality of elongate ribs arranged on the outer surface thereof, and in contact with the inner surface of the outer tube. The elongate ribs may be arranged along the inner tube. Preferably, there are four such elongate ribs spaced angularly by 90° around the outer surface of said inner tube.

Both the flanges and elongate ribs may serve to allow for location of the inner tube centrally in the outer tube during manufacture, and also continue to hold the inner tube in the correct position during transportation, storage, and use.

The inner tube may have an end section which is arranged toward the exposed end of the nozzle. The end section of the inner tube may have a diameter which is greater than that of the rest of the inner tube, thereby providing an enlarged inner tube end section.

The enlarged end section of the inner tube may provide for a close-fit of the end section against the interior surface of the outer tube.

The enlarged end section of the inner tube may have a length in the range from 1 mm to 4 mm. More preferably, said length may be in the range from 1.5 mm to 3 mm. Most preferably, said length may be in the range from 1.7 mm to 2.5 mm.

The enlarged end section may comprise a reduced diameter section so as to provide a stepped enlarged end section. The reduced diameter section is preferably provided adjacent the outlet face of the inner tube. The reduced diameter section may comprise up to approximately half of the enlarged end section of the inner tube. The reduced diameter section makes it easier to assemble the inner tube with the outer tube.

The distance between the external surface of the end section of the inner tube and the inner surface of the outer tube may define a diametrical clearance. This diametrical clearance may be calculated by subtracting the diameters of the end sections of the inner tube from the outer tube. The diametrical clearance may be in the range from 0.10 mm to −0.20 mm. More preferably, said clearance may be in the range from 0.07 mm to −0.17 mm. Most preferably, said distance may be in the range from 0.05 mm to −0.15 mm.

This diametrical clearance may therefore provide for an interference fit between the end sections of the inner tube and the outer tube, and this is indicated where the diametrical clearance values are negative.

It will also be seen that the diametrical clearance between the outer tube and the inner tube around the inclined outlet face would be greater around the inclined outlet of the inner tube. The tight fit of the inner tube to the outer tube may only therefore be maintained around the end section of the inner tube where the inner surface of the outer tube is in close contact with the outer surface of the inner tube.

The end section of the inner tube comprises an inclined outlet face. This inclined outlet face may be formed from a tapered cut. This tapered cut may be arranged such that the size of the end section of the inner tube decreases towards the exposed end.

The inclined outlet face may provide for a segmental circular profile at the exposed end of the inner tube.

The inclined outlet face may have a taper angle being the angle at which the inclined outlet face slopes from the start of the section towards the exposed end of the inner tube and with regard to the horizontal axis. The taper angle may be in the range from 3.00° to 7.00°. More preferably, said taper angle may be in the range from 4.00° to 6.00°. Most preferably, said taper angle may be in the range from 4.50° to 5.60°.

It may also be envisioned that the taper angle is not uniform along the whole length of the inclined outlet face, and may vary. In an embodiment in which the taper angle varies along the inclined outlet face, it will be understood that the taper angle would be an average value along the whole length of the inclined section.

The inclined outlet face may have a taper length being the length of the inner tube from a starting point at which the incline begins, and ending at the exposed end of the inner tube where the incline ends.

The taper length may be in the range from 1.0 mm and 4.0 mm. More preferably, said taper length may be in the range from 1.5 mm to 3.5 mm. Most preferably, said taper length may be in the range from 2.0 mm to 3.0 mm.

The inclined outlet face may comprise an inclined groove. The inclined groove may comprise edge portions which are arranged between the inner and outer tubes, and formed by the inner tube, and a central portion formed by the groove itself.

The inclined groove may have a groove width defined by the distance between the edge portions. The groove width may be in the range from 0.90 mm to 1.50 mm. More preferably, said groove width may be in the range from 1.05 mm to 1.30 mm. Most preferably, said groove width may be in the range from 1.10 mm to 1.20 mm.

The inclined groove may have a groove angle defined by the angle at which the groove slopes from the start of the groove towards the exposed end of the inner tube. The groove angle may be in the range from 35.0° to 10.0°. More preferably, said angle may be in the range from 28.0° to 17.0°. Most preferably, said angle may be in the range from 23.0° to 20.0°.

It will be understood that the tapered groove, if present, would therefore have a greater taper angle than the inclined outlet face described herein.

The inclined groove may have a groove length being the length of the inner tube from a starting point at which the groove begins, and ending at the exposed end of the inner tube where the groove ends. The groove length may be in the range from 1.0 mm to 3.5 mm. More preferably, the groove length may be in the range from 1.3 mm to 2.8 mm. Most preferably, the groove length may be in the range from 1.5 mm to 2.0 mm.

The feature of an inclined groove, if present, provides the further advantage of decreasing the gap between the air outlet and the water outlet at the exposed end of the inner tube. By doing so, it has been found that the atomised water spray quality may be further improved.

It is envisaged that the gap between the bottom of the inclined groove and the centre of the water outlet at the exposed end of the inner tube may be in the range of 0.6 mm to 0.4 mm.

The use of an inclined outlet face at the end of the inner tube allows for the air flow and water flow to be closer together when exiting the nozzle tip. This decrease in the distance between the air flow and water flow is therefore believed to result in better spray quality and spray atomisation.

The distance between the air flow and water flow may be defined and measured as the distance between a lower edge of the inclined outlet face, or inclined groove if present, and the closest circumferential edge point of the water outlet at the exposed end of the inner tube.

For an inner tube having an inclined outlet face, said distance between the air flow and the water flow may be in the range from 0.80 mm to 0.50 mm. More preferably, said distance may be in the range from 0.78 mm to 0.58 mm. Most preferably, said distance may be in the range from 0.72 mm to 0.64 mm.

It will be understood that in an embodiment of the inner tube which also comprises the feature of an inclined groove, said distance may be further reduced. For an embodiment having an inclined groove, said distance between the air flow and the water flow may be in the range from 0.08 mm to 0.22 mm. More preferably, said distance may be in the range from 0.11 mm to 0.19 mm. Most preferably, said distance may be in the range from 0.13 mm to 0.17 mm.

The releasable attachment means may be arranged between the syringe device and nozzle tip. Any suitable releasable attachment means may be used.

In one embodiment, the nozzle tip may have a cap part which may be secured to, or integral with, said outer tube, and said cap part may have said attachment means formed thereon. Said attachment means may comprise a screw-thread provided internally of said cap part, or may comprise bayonet or catch receiving means.

The dental apparatus may also comprise an adaptor, disposed between said nozzle tip and syringe device, said adaptor allowing attachment of said nozzle tip to said device. Thus in the case where an adaptor is present, it is possible for the same nozzle tip to be fitted to different syringe devices by the use of different adaptors, said adaptor may have a cap part with a screw-thread attachment means provided internally thereof, and a screw-thread for engagement with the nozzle tip, or a bayonet or catch means adapted to be received in bayonet or catch receiving means on the nozzle tip.

Said adaptor may be arranged to cooperate with said nozzle tip via securing means, said securing means providing a leak-proof connection between the nozzle tip and adaptor. Preferably said adaptor has a recess therein in which one end of said securing means locates. In this case a seal may be provided to secure and seal said end of said securing means in the recess. The seal may be an 'o' ring or rubber seal or the like.

There may be arranged between the inner tube and the outer tube a sealing means. The sealing means may comprise a moulded seal which is formed around the outer surface of the enlarged end section of the inner tube, and is in contact with the inner surface of the outer tube.

The moulded seal may be formed by a raised bead seal being integral with the inner tube. The moulded seal may be formed on the inner tube around the circumference of enlarged end section. The bead moulded seal is preferably continuous and unbroken.

The moulded seal may be positioned between the start of the inclined outlet face, or inclined groove if present, and the exposed end. If so positioned, the moulded seal would not continue around the edge of the inclined outlet face or inclined groove. The moulded seal may therefore, be located approximately half way along the enlarged end section. Furthermore, the reduced diameter section of the enlarged end section is preferably provided from the outlet face up to the moulded seal In an alternative embodiment the sealing means may comprise an 'o' ring, rubber seal, or the like.

By arranging the sealing means between the outer and inner tubes, said sealing means may provide a more airtight seal between the inner and outer tubes.

Without wishing to be bound by theory, it is believed that the use of a tight fit inner tube combined with an inclined outlet face provides an improved air velocity and atomised water spray quality. The inclined outlet face provides a non-annular air flow which is controlled due to the expanded exit chamber for the air flow path. This change from an annular air flow as seen in the existing tips as seen in patent GB 2213732, to a non-annular airflow as seen in the present invention has been found to be advantageous.

The result of these features may be a change in the velocity of the air jet exiting the nozzle tip, and provision of better spray patterns and atomisation due to the proximity of the water and air flows at the end of the nozzle tip.

All of the features described herein may be combined with any of the above aspects, in any combination.

In order that the present invention may be more readily understood, and to show how embodiments of the same may be carried into effect, reference will now be made, by way of example, to the following description and to the accompanying diagrammatic drawings in which:

FIG. 1 shows a schematic perspective view of a dental apparatus;

FIG. 2 shows a sectional side view of a nozzle tip;

FIG. 3 shows a perspective view of an inner tube;

FIG. 4 shows a partial side view of the inner tube of FIG. 3;

FIG. 5 shows a partial perspective schematic view of the inner tube of FIG. 3;

FIG. 6 shows a schematic end view of a nozzle tip;

FIG. 7 shows a perspective view of an alternative embodiment of an inner tube;

FIG. 8 shows a partial perspective schematic view of the inner tube of FIG. 7;

FIG. 9 shows a partial side view of a further alternative embodiment of an inner tube; and FIG. 10 shows a partial top view of the inner tube of FIG. 9.

Referring now to FIG. 1 there is shown a dental apparatus 10 comprising a nozzle tip 11 for a three-way syringe device 12. The syringe device 12 comprises a body 13 which is connected to a flexible coaxial pipe arrangement 14, itself connected to sources (not shown) of air and water under pressure. Two levers 15, 16 are provided on the body 13 and are operable to allow flow of air, water or air and water through the apparatus 10.

The syringe device 12 has a head 17 which is provided with a snap-fit fitting 18. An adaptor 9 is also provided having a reciprocal snap-fit fitting by means of which fitting the adaptor 9 (and attached nozzle tip 11) can be removably attached to the head 17. The nozzle tip 11 has a bayonet receiving slots on a cap part 19 which can engage with said reciprocal bayonets on the adaptor 9. The nozzle tip 11 may therefore be readily attached and removed from the adaptor 9 by cooperation of the bayonets and bayonet receiving slots.

The nozzle tip 11 comprises an inner tube 20 and an outer tube 21 (both shown on FIG. 2) which form a coaxial tube assembly from the cap part 19 to the air/water jet end 22. Both the inner tube 20 and the outer tube 21 sealingly engage with the co-operating inner tube and outer tube of the adaptor 9, which in turn sealingly engage with the head 17 of the syringe device 12. This ensures that there is no back flow of one fluid medium down the supply pipe of the other fluid medium when the latter is not being used.

The inner tube 20 is formed from plastics material. The outer tube 21 is separately formed from a plastics material and may be moulded integrally with the cap part 19. The nozzle tip 11 is then assembled by inserting the inner tube 20 in to the outer tube 21. By this means, the nozzle tip 11 can be inexpensively produced so that it can be discarded after use of the apparatus 10 on a patient to reduce the risk of cross-infection of any subsequent patient. A new uncontaminated nozzle tip 11 can be readily attached to the head 17 for use of the apparatus 10 on another patient. The nozzle tip 11 may be removed and replaced with the adaptor 9, or alternatively the nozzle tip 11 only may be replaced leaving the adaptor 9 attached to the head 17 for re-use.

Other readily separable attachment means will be readily apparent to persons skilled in the art. For example, the snap-fit fitting and bayonets may be replaced by screw-threads, or a radially outward spring loaded catch which is received in an aperture or outwardly directed recess in the cap part 19, or an internal bore of the cap part 19 may be dimensioned so that the cap part 19 is simply a push fit on a shoulder of the adaptor 9.

Figure 2:
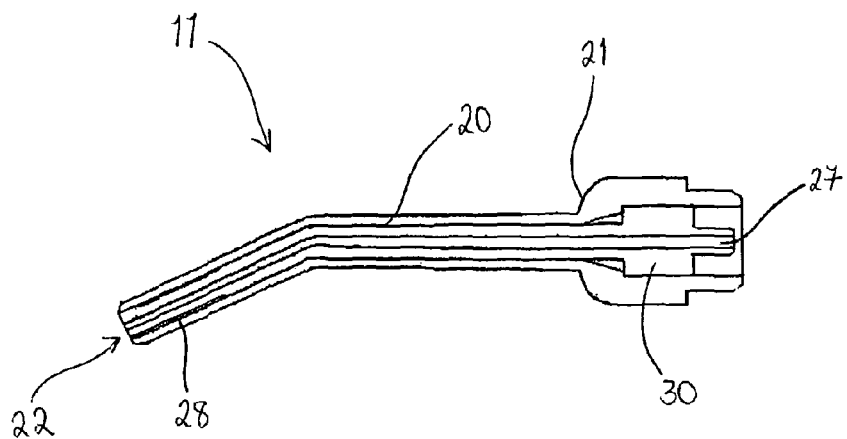

Referring to FIG. 2, there is shown a sectional view of the nozzle tip 11 as shown in FIG. 1. The tip 11 comprises an inner tube 20 and an outer tube 21, both of which are injection moulded. The two components 20, 21 combine to provide separate flow channels for both water and air. Water flows down a central conduit 27 in the inner tube 20, and air travels in the annular area 28 between the inner tube 20 and outer tube 21. The water and air flows exit the end 22 of the tip 11 in order to provide a water jet, air jet, or a combined water/air spray depending on the user's selection.

The tip 11 is mounted to the syringe 12 by an adaptor 9 as shown in FIG. 1.

The inner tube 20 also has four flanges 30 arranged towards the cap 19 end of the nozzle tip 11. These flanges 30 are arranged at 90° on the outer surface of the inner tube 20, and are in contact with the inner surface of the outer tube 21. The flanges 30 protrude radially outward from an enlarged part of the inner tube 20. The flanges 30 have a clearance-fit against the inner surface of the outer tube 21. The flanges 30 provide an axial 'stop' when the nozzle tip 11 is assembled by inserting the inner tube 20 into the outer tube 21. The ends of the flanges 30 are pushed against a stop face at the syringe end of the outer tube 21, and this ensures the correct axial positioning of the inner tube 20 in the outer tube 21 such that the end of the inner tube 20 is flush with the end of the outer tube 21 at end 22 of the nozzle tip 11.

Additionally, the inner tube 20 also has four elongate ribs 29 arranged along a central portion of the nozzle tip 11. The elongate ribs 29 are also arranged at 90° on the outer surface of the inner tube 20, and are also in contact with the inner surface of the outer tube 21. Both the flanges 30 and the elongate ribs 29 enable the inner tube 20 to be correctly centralised in the outer tube 21 during manufacture, and also continue to hold the inner tube 20 in the correct position during transportation, storage, and use.

Figure 3:
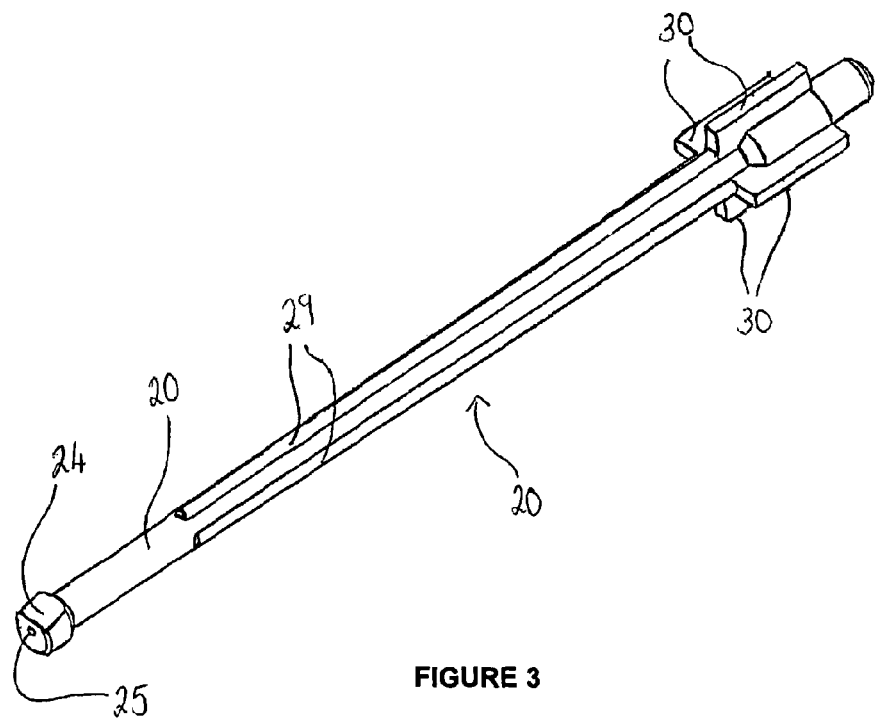

Referring to FIG. 3 there is shown a perspective view of the inner tube 20 from FIG. 2. The inner tube 20 is shown as having flanges 30 arranged at 90° from each other towards one end of the inner tube 20. The inner tube 20 also has elongate ribs 29 arranged along the tube 20 length, and these are formed by integrally moulding during inner tube 20 manufacture.

Figure 4:
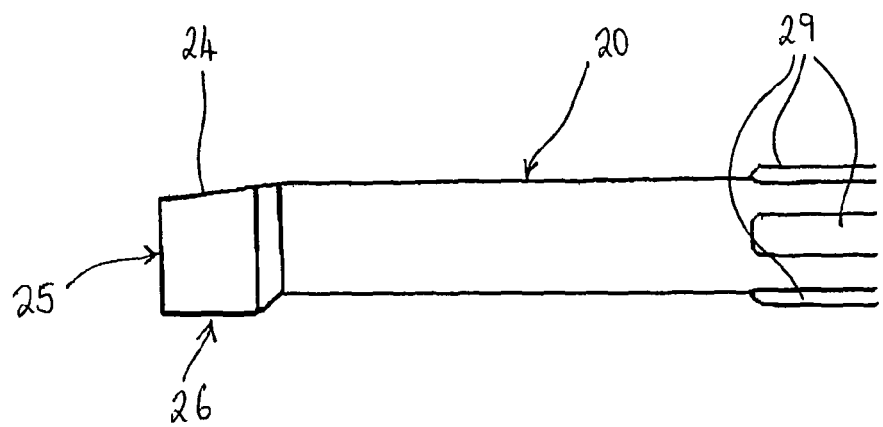

Referring to FIG. 4 there is shown a partial side view of the inner tube 20 from FIGS. 2 and 3. The inner tube 20 comprises an end section 26 having an inclined outlet face 24 arranged on one side thereof. The inclined outlet face 24 is a tapered section in which the taper angles downwards towards the end of the inner tube 20. The rest of the end section 26 of the inner tube 20 is formed with dimensions such that it forms a tight interference fit against the inner surface of the outer tube 21 (not shown in FIG. 4).

In this way the air flow which travels down the area 28 between the inner 20 and outer tubes 21 is directed across the inclined outlet face 24 and exits the tip 11. The air flow can then combine with the water jet which exits the inner tube 20 at a separate exit 25, and which outlet 25 is positioned at the centre of the inner tube 20.

The inner tube 20 also comprises a number of elongate ribs 29 arranged around the exterior surface of the tube 20. There are four elongate ribs 29 arranged at 90° with respect to each other.

Figure 5:
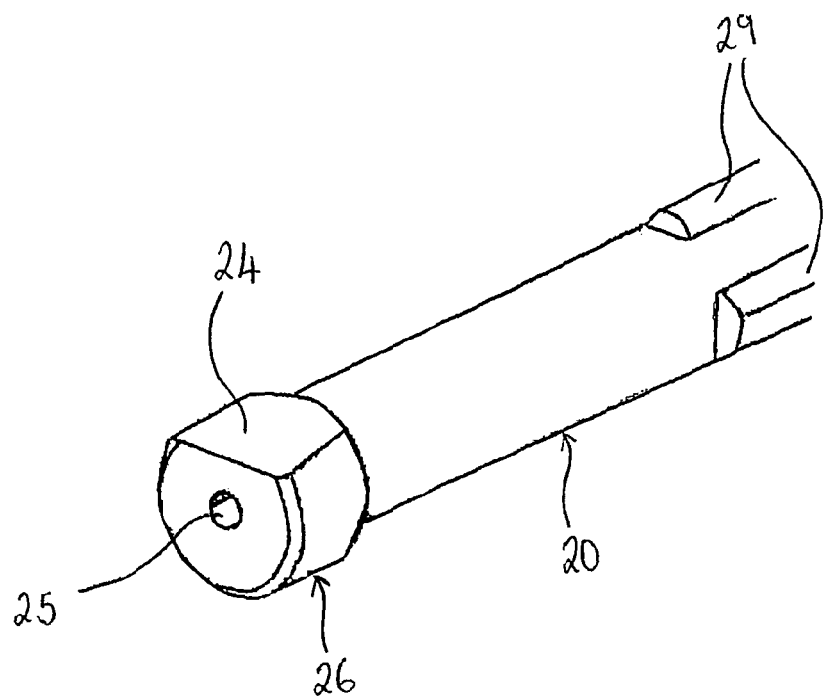

Referring to FIG. 5, there is shown a partial perspective schematic view of the inner tube 20 of FIG. 4. FIG. 5 shows the same feature of the inner tube 20 comprising an inclined outlet face 24 arranged at the end of the tube 20. The air flow would be directed across and out of the tip 11 from this inclined outlet face 24. Additionally, the water jet outlet 25 is shown. The water flows down a conduit which is centrally positioned along the length of the inner tube 20.

It can be seen in FIG. 5 that the inclined outlet face 24 provides for an air flow from the tip 11 which is close to the water flow exiting the outlet 25, and therefore this allows for good mixing of the water and air jets to form an atomised water spray of good quality.

Figure 6:
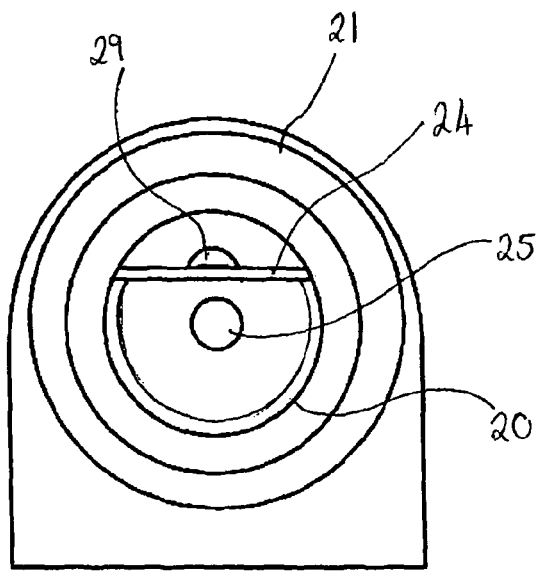

Referring to FIG. 6, there is shown a schematic end view of the nozzle tip 11 of FIG. 2. The nozzle tip 11 is formed from the outer tube 21 and the inner tube 20. Additionally, there is shown the inclined outlet face 24 of the inner tube 20 which allows for air flow from the tip 11. This inclined outlet face 24 provides an exposed end of the inner tube 20 which has a segmental circular shape in profile. The outlet 25 for the water flow from the tip 11 is also shown at the centre of the inner tube 20.

The inner tube 20 is arranged so that it has a tight fit against the outer tube 21 for the non-inclined outlet face. This ensures that the air flow is directed to the inclined outlet face 24 and does not leak out from the tip 11 around the non-inclined outlet face.

Figure 7:
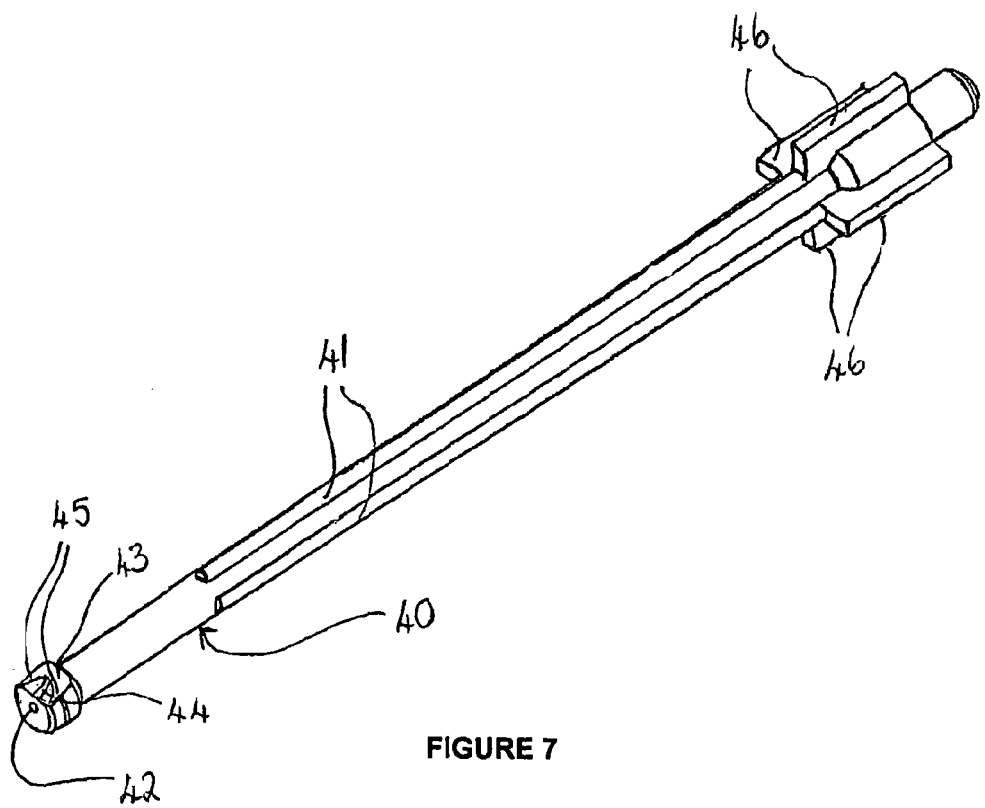

Referring to FIG. 7, there is shown a perspective schematic view of an alternate embodiment of an inner tube 40. Referring to FIG. 8, there is shown a partial perspective schematic view of the inner tube 40 of FIG. 7. This alternate embodiment inner tube 40 can be used with the tip 11, syringe 12, and outer tube 21 as shown in FIGS. 1 to 6.

The inner tube 40 comprises an end section having a inclined outlet face 43 which is similar to that seen in FIGS. 3 to 6. However, the inclined outlet face 43 in this alternate embodiment also comprises an inclined groove 44 with abutments 45 arranged either side. This inclined groove 44 has a increased angle of taper in comparison to that of the inclined outlet face 43.

The outlet 42 for the water flow from the tip is also shown at the centre of the inner tube 40.

The inner tube 40 is also shown with flanges 46 and elongate ribs 41 which are arranged around the exterior surface of the inner tube 40. There are four flanges 46 and four elongate ribs 41 arranged around the inner tube 40, and these are arranged at 90° with respect to each other. These flanges 46 and ribs 41 serve the same function as those shown in the embodiment of FIGS. 2 to 6.

Referring to FIG. 9 there is shown a partial side view of a further alternative inner tube 60. This alternate embodiment inner tube 60 can also be used with the tip 11, syringe 12, and outer tube 21 as shown in FIGS. 1 to 6.

The inner tube 60 comprises an end section 66 having an inclined outlet face 64 arranged on one side thereof. The inclined outlet face 64 is a tapered section as before in which the taper angles downwards towards the end of the inner tube 60. However, as can be seen in FIG. 10, the inclined outlet face 64 in this embodiment also comprises an inclined groove 63 with abutments 65 arranged either side. This inclined groove 63 has an increased angle of taper in comparison to that of the inclined outlet face 64.

The rest of the end section 66 of the inner tube 60 is formed with dimensions such that it forms a tight interference fit against the inner surface of the outer tube 21 (not shown in FIG. 9). However, the end section 66 comprises a moulded seal in the form of a circumferential bead 62 located approximately halfway along the end section 66. The bead 62 is unbroken and continuous except for where the inclined outlet face 64 is cut away. The bead 62 improves the seal between the end section 60 and the inner surface of the outer tube 21.

The end section 66 also provides a reduced diameter section 67 between bead 62 and the free end of the end section 66, so as to provide a stepped end section 66. The reduced diameter section, being located adjacent the free end of the inner tube 60, makes it easier to assemble the inner tube 60 with the outer tube 21.

As before, air flow travels down the area 28 between the inner 60 and outer tube 21, is directed across the inclined outlet face 64 and exits the tip 11. The air flow can then combine with the water jet which exits the inner tube 60 at a separate exit 69, and which outlet 65 is positioned at the centre of the inner tube 60.

Whilst it can be seen that FIGS. 7-8 and 9-10 show alternative inner tubes 40, 60 in which the inclined outlet face 43 and the enlarged head section 66 differ from that shown in FIGS. 3 to 6, it will be appreciated that other variations are also possible.

In order to further understand the invention, experiments were performed, and the results are detailed below.

It will be understood that all tests and physical properties listed have been determined at atmospheric pressure and room temperature (i.e. 20° C.), unless otherwise stated herein, or unless otherwise stated in the referenced test methods and procedures.

Test Methodology

Air Velocity

Air velocity testing was carried out using a small anemometer in order to measure air velocity in units of meters per second (m/s). The anemometer used was the 'JD Skywatch Xplorer 2' which is commercially available. The anemometer was used to determine a maximum velocity achieved over a given time period as this provides more consistent results than measuring an instantaneous velocity where readings may be subject to some degree of variation.

The test methodology comprises a horizontal bar being placed in front of the anemometer to provide a distance marker to ensure all readings were taken at the same distance from the nozzle tip, this was set at 40 mm from the front face of the anemometer. All tests were carried out at an air pressure of 40 psi and a water pressure of approximately 40 psi.

Testing was carried out by spraying air continuously into the anemometer for a period of time (10-20 seconds), during this time the angle of the tip was continually adjusted to ensure the jet of air hit all areas of the fan. On completing the test the anemometer indicated the maximum air velocity achieved over the test period and this was recorded in units of meters per second (m/s).

Spray

Due to subjective nature of the quality of spray and the absence of any easily measurable data, the assessment of the spray performance followed a more empirical approach. Spray quality can be said to be defined by two characteristics:
1. The spread of the spray—i.e. the angle of the conical spray shape produced
2. The level of atomisation—i.e. the spray should be a fine mist with no large water droplets A five category assessment criteria was developed to help identify different types of spray, these were named as follows: None, Poor, OK, Good, and Excellent. For example, an 'Excellent' spray would be one that gives a good, wide angled conical shape to the spray, and is fully atomised throughout. A 'Poor' spray would be one has very narrow spread and contains large visible droplets of water i.e. is not fully atomised. The category 'None' describes where there is no spray at all and a water jet is seen continuing in a straight line.

Spray testing was carried out against a black background in a well-lit area in order to provide better visibility of the spray quality.

Experimental Data

A series of experiments were undertaken to assess the air velocity and spray quality performance of existing tips and tips of the present invention. A desired spray performance would be where the majority of the tips tested exhibited spray quality in the excellent, good, and ok categories. Additionally, it would be desired that the air velocity exhibited by the tips would be above 13.5 m/s.

A number of tips were tested to determine air velocity in accordance with the methods described herein for two types of commercially available syringe, and an average of the values obtained was taken in order to eliminate minor experimental variations. The results obtained are shown in Table 1.

TABLE 1

| | Air velocity values | | | |
|---|---|---|---|---|
| | Air Velocity (m/s) | | | |
| | Syringe A Air pressure 60 psi | Syringe A Air pressure 40 psi | Syringe B Air pressure 60 psi | Syringe B Air pressure 40 psi |
| Manufacturer Tip | 19.8 | 14.3 | 18.9 | 14.8 |
| Standard Pro-Tip | 14.2 | 10.8 | 13.0 | 10.1 |
| Tip A | 23.1 | 16.4 | 19.9 | 15.1 |
| Tip B | 20.3 | 15.1 | 17.7 | 13.9 |
| Tip C | 21.3 | 14.1 | 19.7 | 13.8 |

Syringes A and B were commercially available syringes.

Manufacturer's Tip—This tip is a reusable standard tip available from the syringe manufacturer. The tip comprises two separate circular channels, one for air and one for water. At the exposed end of the tip each channel has a circular exit.

Standard Pro-Tip—This was an existing Pro-Tip device (as shown in GB 2213732) which was invented by the current applicant. The nozzle has an inner tube and an outer tube. The inner tube is not tight fit against the outer tube, and the inner tube comprises two small notches, each arranged at opposite sides around the circumference of the end section of the inner tube.

Tip A—This was a tip of the present invention having an inclined outlet face with a taper angle of 5.71° to 7.97°, a diametrical clearance value of 0.05 mm to −0.15 mm, and a height of the exposed end of the inner tube of 2.55 mm to 2.65 mm. The tip had an inner tube and an outer tube with a tight interference fit.

Tip B—This was a tip of the present invention having an inclined outlet face with a taper angle of 4.06° to 5.20°, a diametrical clearance value of 0.07 mm to −0.08 mm, and a height of the exposed end of the inner tube of 2.65 mm to 2.70 mm. The tip had a tight interference fit and an inclined outlet face at the exposed end of the inner tube. Tip B had a reduced taper angle when compared to Tip A, and a larger diametrical clearance than Tip A.

Tip C—This was a tip of the present invention having an inclined outlet face with a taper angle of 4.57° to 5.48°, a diametrical clearance value of 0.05 mm to −0.15 mm, and a height of the exposed end of the inner tube of 2.66 mm to 2.70 mm. The tip also comprised an inclined groove having an angle of 21.9°, and having a distance between the water and air jets of 0.15 mm. The tip had a tight fit between the inner tube and the outer tube at the end section.

The tips were further tested to determine spray quality in accordance with the methods described herein. A number of tips were used in order to eliminate minor experimental variations. The percentages of tip samples which fit in to the defined spray quality categories are shown in Table 2.

All tips were tested using the Syringe B and at a water pressure of 40 psi and an air pressure of 40 psi.

TABLE 2

Spray Quality Values

| | Spray Performance (%) | | |
|---|---|---|---|
| | Excellent | Good | OK |
| Standard Pro-Tip | 0 | 0 | 0 |
| Tip A | 0 | 25 | 35 |
| Tip B | 0 | 25 | 25 |
| Tip C | 57 | 29 | 7 |

The remaining percentages of each of the tip samples had a spray performance categorised as poor or none.

For all three tips of the present invention (i.e. Tip A, B, and C) the values of air velocity at both higher and lower pressures, and the spray quality are significantly improved when compared to existing tips such as the Standard Pro-Tip.

It can be seen for Tip A that the air velocity results are very good and the velocities exceed that of the existing Pro-Tip syringe and the manufacturer's syringe. Additionally, the spray velocity results for Tip A are significantly improved in comparison to the existing Pro-Tip. Tip A produces excellent performance, both in terms of air velocity and spray at both lower and higher pressures on different syringe types.

It can be seen for Tip B that the air velocity results are very good and the velocities exceed that of the existing Pro-Tip syringe and the manufacturer's syringe. The spray velocity results are also significantly improved in comparison to the existing Pro-Tip. The majority of Tip B tips were found to have a spray quality of at least 'OK' or better. Tip B provided a good compromise between spray quality and air velocity, and produced excellent performance both in terms of air velocity and spray on different syringe types at different pressures.

Tip C, which additionally comprised an inclined groove, again provided air velocity results at different pressures when compared to the existing Pro-Tip. Additionally, the spray quality results shown in Table 2 indicate excellent spray quality with over 50% of the tips having spray quality in the excellent category and a further 36% of the tips with spray quality of Good or Ok.

It is to be understood that the invention is not to be limited to the details of the above embodiments, which are described by way of example only. Many variations are possible.

The invention claimed is:

1. A nozzle tip for a three-way syringe device, said nozzle tip comprising a co-axial tube assembly having an attachment end configured for releasable attachment of said nozzle tip to a syringe device, and wherein said tube assembly comprises an outer tube and an inner tube, said inner tube comprising an exposed end section with a water outlet and a hollow conduit extending along its length providing for water flow from the attachment to the water outlet, the inner and outer tubes providing an annular air flow area therebetween, the inner tube having an enlarged end section comprising a single inclined outlet face, and wherein air flow travels through the annular air flow area between the inner and outer tubes and is directed across the single inclined outlet face of the enlarged end section to exit the nozzle tip, wherein the inner tube has a tight interference fit against an interior surface of the outer tube at the enlarged end section, and the interference fit extends around the enlarged end section except for the single inclined outlet face, and the single inclined outlet face and the interior surface of the outer tube form therebetween an exit chamber for the air flow, which exit chamber increases in cross-sectional area going from an inlet end to an outlet end of the exit chamber.

2. The nozzle tip according to claim 1, wherein the outer tube and the inner tube are separately manufactured and subsequent assembled including insertion of the inner tube into the outer tube.

3. The nozzle tip according to claim 1, wherein an exposed end of the inner tube is level with an exposed end of the outer tube.

4. The nozzle tip according to claim 3, wherein a height of the exposed end of the inner tube from the single inclined outlet face to a furthermost circumferential point of the inner tube is from approximately 2.00 mm to approximately 3.20 mm.

5. The nozzle tip according to claim 1, wherein an internal diameter of the outer tube is from approximately 3.00 mm to approximately 3.50 mm.

6. The nozzle tip according to claim 1, wherein the enlarged end section of the inner tube has a length from approximately 1 mm to approximately 4 mm.

7. The nozzle tip according to claim 1, wherein the enlarged end section comprises a reduced diameter section adjacent the single inclined outlet face of the inner tube so as to provide a stepped enlarged end section.

8. The nozzle tip according to claim 1, wherein the single inclined outlet face is formed of a tapered cut arranged such that the enlarged end section of the inner tube decreases in size towards an exposed end of the inner tube.

9. The nozzle tip according to claim 8, wherein the single inclined outlet face has a taper angle sloping towards the exposed end of the inner tube and with regard to a longitudinal axis of the nozzle tip from approximately 3.00° to approximately 7.00°.

10. The nozzle tip according to claim 8, wherein the single inclined outlet face comprises an inclined groove comprising edge portions which are arranged between the inner and outer tubes, and formed by the inner tube, and a central portion formed by the inclined groove itself.

11. The nozzle tip according to claim 10, wherein the inclined groove has a groove width defined by a distance between the edge portions from approximately 0.90 mm to approximately 1.50 mm.

12. The nozzle tip according to claim 10, wherein the inclined groove has a groove angle at which the inclined groove slopes towards the exposed end of the inner tube from approximately 10.02° to approximately 35.0°.

13. The nozzle tip according to claim 10, wherein the inclined groove has a groove length from approximately 1.0 mm to approximately 3.5 mm.

14. The nozzle tip according to claim 10, wherein a distance between a bottom of the inclined groove and a centre of the water outlet at the exposed end of the inner tube is approximately 0.4 mm to approximately 0.6 mm.

15. The nozzle tip according to claim 1, wherein a sealing means is arranged between the inner tube and the outer tube comprising a moulded seal which is formed around an outer surface of the enlarged end section of the inner tube and is in contact with the interior surface of the outer tube.

16. A dental apparatus comprising a nozzle tip for a three-way syringe device according to claim 1.

\* \* \* \* \*